United States Patent [19]

Kino et al.

[11] Patent Number: 5,376,538
[45] Date of Patent: Dec. 27, 1994

[54] **PROCESS FOR PRODUCING L-THREONINE WITH STRAINS OF *E COLI* RESISTANT TO PHENYLALANINE AND LEUCINE**

[75] Inventors: Kuniki Kino; Junichi Takano; Kazuyuki Okamoto; Yoshiyuki Kuratsu, all of Hofu, Japan

[73] Assignee: Kyowa Hakko Kogyo Co., Ltd., Tokyo, Japan

[21] Appl. No.: 160,668

[22] Filed: Dec. 2, 1993

Related U.S. Application Data

[63] Continuation of Ser. No. 940,394, Sep. 3, 1992, abandoned.

[30] Foreign Application Priority Data

Sep. 4, 1991 [JP] Japan .................................. 3-224259

[51] Int. Cl.$^5$ .............................................. C12P 13/08
[52] U.S. Cl. .................................. 435/115; 435/252.8
[58] Field of Search .............................. 435/115, 252.8

[56] References Cited

.U.S. PATENT DOCUMENTS 4,996,147 2/1991 Furukawa ........................... 435/115
5,017,483 5/1991 Furukawa ........................... 435/115

FOREIGN PATENT DOCUMENTS 0445830 9/1991 European Pat. Off. .
5106752 3/1976 Japan .
0037886 3/1979 Japan .................... 435/115
5610037 3/1981 Japan .
2234686 9/1990 Japan .

OTHER PUBLICATIONS

White, P. J., "The Regulation of Diaminopimelate Decarboxylase Activity in *Escherichia coli* strain w", *J. Gen. Microbiol.*, 96 pp. 51–62 1976.

Patte, J. C. et al., "Effects Inhibiteurs Cooperatifs de la L–Lysime and D'autrs Amino Acids sur une asparto Kinase de *Escherichia coli*," BBA, vol. 99 pp. 523–530, 1965.

*Primary Examiner*—Marian Knode
*Attorney, Agent, or Firm*—Antonelli, Terry, Stout & Kraus

[57] ABSTRACT

Disclosed is a process for producing L-threonine, which comprises culturing an L-threonine-producing microorganism belonging to the genus Escherichia and having a resistance to at least one of L-phenylalanine and L-leucine in a medium until L-threonine is produced and accumulated in the culture, and recovering L-threonine therefrom.

1 Claim, No Drawings

PROCESS FOR PRODUCING L-THREONINE WITH STRAINS OF E COLI RESISTANT TO PHENYLALANINE AND LEUCINE

This application is a continuation application of application Ser. No. 940,394, filed Sept. 3, 1992 abandoned.

BACKGROUND OF THE INVENTION

The present invention relates to a process for producing L-threonine by fermentation. L-threonine is not only useful as a medicament such as amino acid preparations but also utilizable as an additive for animal feed.

With respect to the fermentation process for production of L-threonine by use of a microorganism belonging to the genus Escherichia, various processes have been known; for example, a process using a microorganism having a borrelidin sensitivity (Japanese Published Examined Patent Application No. 6752/76), a process using a microorganism requiring diaminopimelic acid and methionine for growth and of which threonine biosynthesis system is resistant to feedback inhibition of threonine (Japanese Published Examined Patent Application No. 10037/81), a process using a microorganism having a resistance to at least one of rifampicin, lysine, methionine, aspartic acid and homoserine, or a decreased ability to degrade L-threonine (Japanese Published Unexamined Patent Application No. 273487/88, U.S. Pat. No. 5,017,483), a process using a microorganism having a resistance to at least one of L-serine and ethionine (Japanese Published Unexamined Patent Application No. 259088/91, European Publication No. 445830), etc.

However, the known processes are still insufficient in efficiency of the production of L-threonine. It is therefore an object of the present invention to provide a process for producing L-threonine, in higher yield and at lower cost.

SUMMARY OF THE INVENTION

According to the present invention, provided is a process for producing L-threonine which comprises culturing an L-threonine-producing microorganism belonging to the genus Escherichia and having a resistance to at least one of L-phenylalanine and L-leucine in a medium until L-threonine is produced and accumulated in the culture and recovering L-threonine therefrom.

DETAILED DESCRIPTION OF THE INVENTION

In the present invention, any microorganism can be used, so long as it belongs to the genus Escherichia, has a resistance to at least one of L-phenylalanine and L-leucine and is capable of producing L-threonine.

The suitable microorganism used in the present invention can be obtained by subjecting L-threonine-producing microorganisms belonging to the genus Escherichia to the conventional mutagenesis such as treatment with N-methyl-N'-nitro-N-nitrosoguanidine and X-ray irradiation, spreading the resulting microorganisms on a minimum medium containing L-phenylalanine or L-leucine, and picking up colonies grown on the minimum medium. Selection of the desired mutant strain is efficiently performed by using the minimum medium containing L-lysine or a salt thereof such as hydrochloride of L-lysine in an amount of one to 10 g/l. The suitable microorganism used in the present invention may also be obtained by endowing a microorganism belonging to the genus Escherichia and having a resistance to at least one of L-phenylalanine and L-leucine which microorganism is derived from a wild strain, with nutrient auxotrophy, threonine metabolism antagonist-resistance, etc. for imparting L-threonine productivity. Preferred examples of the suitable microorganism are Escherichia coli H-8309 and H-8311.

A specific example of obtaining the preferred strains is described below:

A diaminopimelic acid non-auxotrophic strain, Escherichia coli H-7700 was derived from diaminopimelic acid-auxotrophic strain Escherichia coli H-4581 (FERM BP-1411) having a methionine-requirement, an α-amino-β-hydroxyvaleric acid-resistance, a decreased ability to degrade L-threonine, a rifampicin-resistance, a lysine-resistance, a methionine-resistance, a homoserine-resistance and an aspartic acid-resistance. Further, Escherichia coli H-7700 was endowed with a resistance to L-serine and ethionine to obtain Escherichia coli H-7729 (FERM BP-2792). Escherichia coli H-7729 was subjected to a conventional mutation treatment with N-methyl-N'-nitro-N-nitrosoguanidine (0.2 mg/ml, 30° C., 30 minutes), and then spread on a minimum medium (5 g/l glucose, 2 g/l $NH_4Cl$, 2 g/l $KH_2PO_4$, 0.1 g/l $MgSO_4 \cdot 7H_2O$, 20 mg/l $FeSO_4 \cdot 7H_2O$, 50 mg/l DL-methionine, 2% agar, pH 7.2) containing 10 g/l L-phenylalanine and 3 g/l L-lysine hydrochloride. After culturing at 30° C. for 2 to 6 days, larger colonies grown were picked up as the strain having resistance to L-phenylalanine and subjected to the L-threonine production test to select strains having L-threonine-producing ability greater than that of the parent strain. Among the thus selected strains is Escherichia coli H-8311.

Escherichia coli H-8309 having a resistance to L-leucine was obtained in a manner similar to the procedure for obtaining H-8311 strain except that H-7700 strain was used as the parent strain in place of H-7729 strain, and that L-leucine (6 g/l) was contained in the aforesaid minimum medium in place of L-phenylalanine.

The H-8311 and H-8309 strains thus obtained were deposited on Aug. 21, 1991 in the Fermentation Research Institute, Agency of Industrial Science and Technology, 1–3, Higashi 1 chome Tsukuba-shi Ibaraki-ken 305, Japan under the Budapest Treaty with accession numbers FERM BP-3520 and FERM BP-3519, respectively.

With respect to H-8311 and H-8309 strains, degrees of resistance to L-phenylalanine and L-leucine were examined, as compared to that of the corresponding parent strain. The degree of resistance was expressed in terms of degree of growth. The mutant strains and the parent strains each were cultured for 24 hours on a complete medium (10 g/l trypton, 5 g/l yeast extract, 10 g/l NaCl, 2% agar, pH 7.5) in a slant. The cultured strains were suspended in a sterilized water. The obtained suspension was spread on a minimum medium (5 g/l glucose, 2 g/l $NH_4Cl$, 2 g/l $KH_2PO_4$, 0.1 g/l $MgSO_4 \cdot 7H_2O$, 20 mg/l $FeSO_4 \cdot 7H_2O$, 50 mg/l DL-methionine, 2 g/l L-lysine hydrochloride, 2% agar, pH 7.2) containing L-phenylalanine and L-leucine in the amounts shown in Table 1 and culturing was carried out at 30° C. for 72 hours. The results are shown in Table 1.

TABLE I

| Amount (g/l) | Strain H-7729 | H-8311 | H-7700 | H-8309 |
|---|---|---|---|---|
| Phe | | | | |
| 0 | + | + | + | + |
| 1 | ± | + | ± | + |
| 10 | − | + | − | ± |
| Leu | | | | |
| 0 | + | + | + | + |
| 1 | ± | + | ± | + |
| 6 | − | + | − | + |

+: sufficient growth
±: moderate growth
−: no growth

In the production of L-threonine using the microorganism of the present invention, any conventional method for culturing bacteria is applicable. As the medium, any of a synthetic medium and a natural medium may be used so long as it suitably contains carbon sources, nitrogen sources, inorganic substances and other nutrients required for the strains used.

As the carbon source, carbohydrates such as glucose, fructose, lactose, molasses, cellulose hydrolyzate, hydrolyzate of crude sugar, starch hydrolyzate, etc.; and organic acids such as pyruvic acid, acetic acid, fumaric acid, malic acid, lactic acid, etc. can be used. Depending upon assimilability of the microorganism, glycerine, alcohols such as ethanol, etc. can also be used.

As the nitrogen source, ammonia, ammonium salts of inorganic or organic acids, such as ammonium chloride, ammonium sulfate, ammonium acetate, ammonium phosphate, etc.; amines and other nitrogen-containing compounds, peptone, meat extract, corn steep liquor, casein hydrolyzate, soybean cake hydrolyzate, various cultured cells and their digested product, etc. can be used.

As the inorganic substances, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. can be used.

Culturing is carried out under aerobic conditions, e.g. by shaking culture, agitation submerged culture, etc. at a temperature of 20° to 40° C., preferably 25° to 38° C. The pH of the medium is in the range of 5 to 9, and is preferably maintained at around neutrality. The pH is adjusted with calcium carbonate, inorganic or organic acids, alkaline solutions, ammonia, a pH buffer agent or the like. Usually, after culturing for 2 to 7 days, L-threonine is accumulated in the culture.

After the completion of the culturing, precipitates such as cells, etc. are removed from the culture by means of centrifugation, etc. By using ion exchange treatment, concentration, salting out, etc. in combination, L-threonine can be recovered from the culture.

Hereafter the present invention is illustrated by the following Example.

EXAMPLE 1

Production test of L-threonine

L-threonine production test is carried out by culturing the above-mentioned mutant strains. Escherichia coli H-8311 and its parent strain Escherichia coli H-7729, and Escherichia coli H-8309 and its parent strain Escherichia coli H-7700 each were cultured with shaking at 30° C. for 16 hours in a seed medium (pH 7.4) containing 20 g/l glucose, 10 g/l peptone, 10 g/l yeast extract and 2.5 g/l NaCl. 100 ml of the resulting seed culture was transferred to 1 liter of a fermentation medium having the following composition charged in a 2 l-jar fermentor and culturing was carried out at 30° C. with stirring at 800 rpm and an aeration rate of 1 liter/min for 80 hours. During the culturing, pH control and supply of nitrogen source were made by aqueous ammonia, whereby the pH was kept at about 6.5±0.2, and glucose was supplied at an appropriate time. After the completion of the culturing, the amount of L-threonine accumulated was quantitatively determined by high performance liquid chromatography. The results are shown in Table 2.

Composition of fermentation medium:

40 g/l glucose, 12 g/l $(NH_4)_2SO_4$, 2 g/l $KH_2PO_4$, 0.1 g/l $MgSO_4.7H_2O$, 5 g/l corn steep liquor, 0.3 g/l DL-methionine, (pH 7.4)

One liter of the L-threonine-containing culture obtained by culturing H-8311 strain was centrifuged (3000 rpm, 10 minutes) to remove the cells and other impurities therefrom. The thus obtained supernatant was passed through a column packed with strongly acidic cationic ion exchange resin DIAION SKIB (type H+; product of Mitsubishi Kasei Corporation, Japan) to adsorb L-threonine thereon. The column was washed with water, and subjected to elution with 0.5N aqueous ammonia to collect L-threonine fractions. The collected fractions were concentrated and ethanol was added to the concentrate. By storing the mixture under cooling, 39.5 g of L-threonine crystals having purity of 98% or higher was obtained.

TABLE 2

| Strain | L-Threonine (g/l) |
|---|---|
| H-7700 | 3.4 |
| H-8309 | 10.4 |
| H-7729 | 37.2 |
| H-8311 | 48.7 |

What is claimed is:

1. A process for producing L-threonine which comprises culturing an L-threonine-producing microorganism belonging to the genus Escherichia and having a resistance to at least one of L-phenylalanine and L-leucine in a medium until L-threonine is produced and accumulated in the culture, and recovering L-threonine therefrom; wherein said microorganism is Escherichia coli FERM BP-3519 or Escherichia coli FERM BP-3520.

* * * * *